United States Patent

Heikkilä

[11] Patent Number: 5,810,722
[45] Date of Patent: Sep. 22, 1998

[54] METHOD AND DEVICE FOR DETERMINING THRESHOLD VALUES FOR ENERGY METABOLISM

[75] Inventor: Ilkka Heikkilä, Oulu, Finland

[73] Assignee: Polar Electro Oy, Kempele, Finland

[21] Appl. No.: 817,219

[22] PCT Filed: Oct. 11, 1995

[86] PCT No.: PCT/FI95/00565

§ 371 Date: Jun. 23, 1997

§ 102(e) Date: Jun. 23, 1997

[87] PCT Pub. No.: WO96/11630

PCT Pub. Date: Apr. 25, 1996

[30] Foreign Application Priority Data

Oct. 13, 1994 [FI] Finland .................................. 944824

[51] Int. Cl.⁶ .................................................. A61B 5/0205
[52] U.S. Cl. ........................................ 600/300; 600/520
[58] Field of Search .................................. 600/300, 520, 600/509, 521

[56] References Cited

U.S. PATENT DOCUMENTS

| | | |
|---|---|---|
| 4,202,350 | 5/1980 | Walton . |
| 4,281,663 | 8/1981 | Pringle ..................... 128/689 |
| 4,566,461 | 1/1986 | Lubell et al. ............. 128/668 |
| 4,930,518 | 6/1990 | Hruhesky . |
| 5,297,558 | 3/1994 | Acorn et al. . |
| 5,456,262 | 10/1995 | Birnbaum ................ 128/707 |

FOREIGN PATENT DOCUMENTS

| | | |
|---|---|---|
| 399 449 B | 5/1995 | Austria . |
| 3439238 A1 | 5/1985 | Germany . |
| WO 92/06632 | 4/1992 | WIPO . |
| WO 92/22245 | 12/1992 | WIPO . |

OTHER PUBLICATIONS

Treese et al., "Ventilation and Heart Rate Response During Exercise In Normals: Relevance For Rate Variable Pacing", PACE, vol. 16, pp. 1693–1700 (Aug. 1993).

Primary Examiner—Marvin M. Lateef
Assistant Examiner—Eleni Mantis Mercader
Attorney, Agent, or Firm—Hoffmann & Baron, LLP

[57] ABSTRACT

The invention relates to a method and a device for determining threshold values for a person's energy metabolism. A testee is subjected to a gradually increasing stress in order to obtain the threshold values for his energy metabolism. The pulse rate of the testee is measured during the performance, the pulse shape of an ECG signal caused by the pulse is analyzed in order to determine the timing point of the ECG signal corresponding to each pulsation and in order to determine the intervals between the timing points of success of ECG signals. The respiratory frequency of the testee is calculated on the basis on the variations in the intervals between the timing points of the ECG signals. The respiratory frequency of the testee is calculated as a function of the pulse rate during the performance, where the respiratory volume is estimated on the basis of the degree of the variation in the timing points of the ECG signals, and ventilation is calculated as a function of the pulse rate on the basis of the respiratory frequency calculated during the performance and the estimated respiratory volume. At least one threshold value for the energy metabolism of the testee is determined on the basis of the respiratory frequency or the ventilation and the pulse rate.

7 Claims, 3 Drawing Sheets

METHOD AND DEVICE FOR DETERMINING THRESHOLD VALUES FOR ENERGY METABOLISM

BACKGROUND OF THE INVENTION

1. Field of the Invention

The invention relates to a method and a device for determining threshold values for energy metabolism, in which method a testee is subjected to a gradually increasing stress in order to obtain the threshold values for his energy metabolism.

2. Description of the Prior Art

When a runner starts running, the lactic acid content of his blood first tends to drop below the original level. This is due to a faster circulation and the fact that the lactic acid elimination processing improves with muscle work. After this, if the speed of running is steadily increased, the lactic acid content begins to rise linearly with respect to the stress. The work rate at which the lactic acid content reaches its original value, and the corresponding levels of vital functions, such as pulse rate and oxygen consumption, are called an aerobic threshold.

At work rates that are lower than the aerobic threshold, energy is produced aerobically, i.e. fats and carbohydrates are burned by means of oxygen. At work rates exceeding the aerobic threshold, energy is in turn produced to a greater and greater extent anaerobically, i.e. without oxygen, so that more and more lactic acid is correspondingly formed in the tissues. Simultaneously, the proportion of fat consumption in the production of energy decreases rapidly and carbohydrates become the primary source of energy.

Increasing the level of performance further finally results in a situation in which the system of the athlete can no longer process the amount of lactic acid that develops in the energy production. The disturbance of the balance is detected as a sharply rising lactic acid content of blood and as a simultaneous clear increase in ventilation. This critical level of performance that is significant for training is called an anaerobic threshold.

In physiology, an aerobic threshold is thus defined as the stress level at which the lactic acid content in the blood of an athlete or a fitness enthusiast exceeds the level of rest, or at which the ventilation increases faster than previously with respect to the increasing stress. Pulse rate measurement can be utilized in estimating the work rate of an athlete or a fitness enthusiast, since the pulse rate and the work rate are linearly dependent on each other.

An anaerobic threshold, on the other hand, denotes the stress level at which the lactic acid content of blood starts rising rapidly and the ventilation begins to increase clearly faster than the stress or the oxygen consumption.

Determining the aerobic and the anaerobic threshold is primarily used in the training of endurance athletes in order to determine a suitable training efficiency and to monitor the effects of the training. Similarly, for example the optimum training efficiency of a dieter can be determined by means of the thresholds. The aerobic and anaerobic threshold are nowadays determined in special test laboratories by means of a so-called maximum stress test. The test is started with a small stress. The stress is increased step by step every 2 to 3 minutes without any pauses up to the maximum level of performance. During the last 30 seconds of each stress, a blood sample is taken from the testee in order to determine the lactic acid level, or alternatively, the ventilation is measured. The threshold values determined by means of lactic acid and ventilation are usually very close to each other. The results are strongly influenced by the manner of stressing, the rate at which the stress is increased, and the stress levels used, wherefore different physical stress situations, such as a treadmill and an ergometer, provide different threshold values.

Ventilation, i.e. the respiratory volume per minute (VE), is obtained by multiplying the respiratory volume per time (TV) by the respiratory frequency (fr).

$$VE = fr \cdot TV \tag{1}$$

Formula (1) shows that ventilation can be increased both by increasing the respiratory volume per time and by increasing the respiratory frequency. They both change when the stress on the system increases. The respiratory volume per time is in most cases, but not always, almost linearly dependent on the stress level. In some cases, the sharp increase in ventilation occurring after the anaerobic threshold is mainly due to the increase in the respiratory volume per time. However, a point of vertical intersection can almost always be seen in the respiratory frequency at the anaerobic threshold. On the other hand, the aerobic threshold of unfit testees cannot always be determined due to low aerobic strength and poor ability to process lactic acid.

As stated above, known methods and devices for determining threshold values for energy metabolism are based on difficult lactic acid and ventilation measurements wherein blood sampling and expensive laboratory equipment are central. The purpose of the present invention is to provide such a method and a device for determining threshold values for energy metabolism that are simple, reliable and require no trained medical personnel in order to be used.

OBJECTS AND SUMMARY OF THE INVENTION

The method and the device according to the invention are characterized by what is disclosed in the claims below. The invention is based on the idea that signals provided by accurate pulse rate measurement contain information on the basis of which conclusions concerning the respiratory arrythmia can be drawn, the strength of the arrythmia depending both on the depth of respiration and the respiratory frequency. This in turn enables in principle the determination of the threshold values for energy metabolism on the basis of mere pulse rate measurement in the manner described above. The present pulse rate measuring devices that average the pulse rate do not provide sufficient accuracy.

When the heart contracts, it causes a series of electric pulses that can be measured everywhere in the body. The measurement and analysis of such a signal is called electrocardiography (ECG). The signal itself is called an ECG signal. Components resulting from the different functional periods of the heart can be distinguished from an ECG signal. These components are called P, Q, R, S, T and U waves (cf. FIG. 1). A P wave is caused by the contraction of the atria. When the atria contract, the ventricles are filled with blood. The most discernible feature of an ECG signal is its maximum, i.e. the R peak, which has a shape that is determined by a so-called QRS complex formed by the peaks of three waves, and which develops when the ventricles contract. The right ventricle then pumps blood from the veins to the lungs and the left ventricle from the lungs to the arteries. The repolarization of the ventricular muscles causes a T wave, which is lower and more even than the R peak. Sometimes it is also possible to discern a U wave the origin of which is unclear. The intervals between the waves depend on the rate at which a nervous impulse proceeds in the heart. The operation of the heart synchronizer, i.e. the sinus, is not visible in an ECG signal.

The ECG signal of a healthy person has the amplitude of 1 to 2 mV when measured from the surface of the skin. For example the R peak is given the amplitude value of 1.6 mV and the duration of 90 ms in the literature, whereas the corresponding values for the P wave are 0.25 nV and 110 ms. When the pulse accelerates as a result of stress, the durations and amplitudes of the different components in the ECG signal remain almost the same. It is therefore known that the exact measurement of the pulse rate and the related phenomena is possible by analysing the ECG signal of the pulse. As stated above, sufficient accuracy is not obtained, however, with the present wireless pulse rate measuring devices that average the pulse rate and that are mostly intended for sports and fitness.

The easiest starting point for accurately determining the timing point of the ECG signal is the detection of the QRS complex. In an interference-free situation, the QRS complex can be detected fairly simply with a peak detector. In order to reduce the interference occurring in practical situations, some kind of filtration is utilized in accurate analyses. The following examples can be provided:

bandpass filtration with which the frequencies contained in the QRS complex are accentuated, and in which the QRS complexes are separated from the filtered signal utilizing a non-linear interference rule based on a discernible property of the QRS complex, such as rate of rise, amplitude, etc.;

matched filtration wherein the QRS complex is modelled for example in a FIR filter with filter coefficients, and cross-correlation with the incoming signal and the QRS correlation that is provided as coefficients is calculated;

a pattern recognition method wherein the signal to be processed is parametrized into a series of peaks of different widths and heights. Pattern recognition aims at recognizing from the ECG signal the peaks resulting from the functional periods of the heart. The method is also applicable in the detection of timing points other than those based on the QRS complex.

The development of microprocessors enables the implementation of more and more complicated digital filter structures without any increase in the size and the current consumption of the device. The methods, shortly listed above, for recognizing timing points thus constitute only some of the feasible algorithms, and more methods are being developed continuously.

In practice, the individual differences between people, the various other adjustment mechanisms of the body, and different conditions make it difficult to draw reliable conclusions, despite accurate measurements, wherefore it is preferable to apply the method according to the invention to the observation of one and the same individual under carefully standardized conditions. Since it is in any case necessary to monitor the condition and work rate of an athlete during a training season, and since it is easy to use standardized conditions and methods in sports training, the desired training efficiency can be maintained by means of continuous monitoring of the pulse rate when the pulse rate values corresponding to the thresholds for energy metabolism are known.

BRIEF DESCRIPTION OF THE DRAWINGS

In the following, the invention will be described in greater detail by means of examples and with reference to the accompanying drawings, in which.

DETAILED DESCRIPTION OF THE PREFERRED EMBODIMENTS

Figure 1:
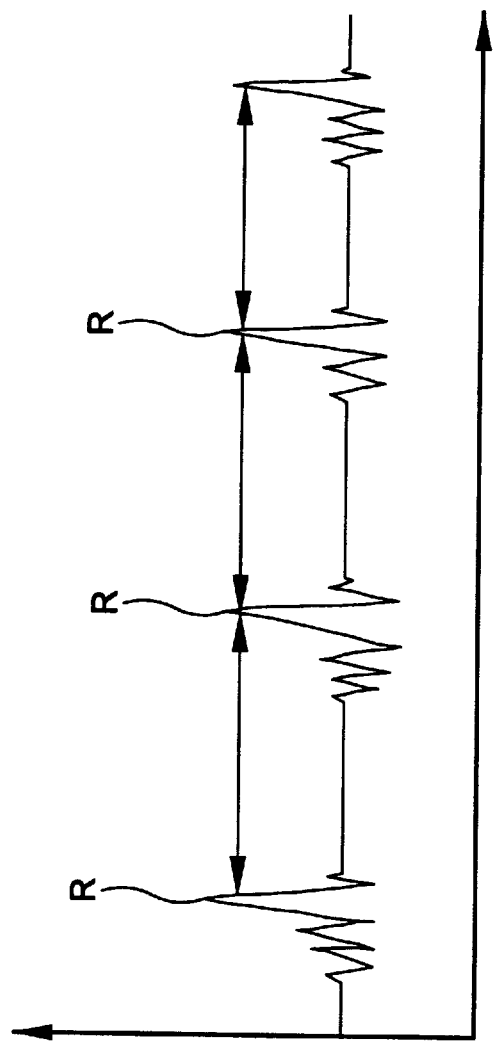
FIG. 1 shows a shape of an ECG signal caused by a pulse.

FIG. 1 shows a typical ECG signal caused by a pulse. The aforementioned P, Q, R, S, T and U waves can be recognized from each signal by means of accurate measurement. The peak value R represents the maximum of the ECG signal. According to an embodiment of the invention, the variations of the time intervals between these peaks, i.e. the so-called R—R variation, are determined, and the respiratory frequency curve of the testee can be calculated on the basis of this variation as a function of the pulse rate.

Due to the variation in the sympathetic-parasympathetic balance of the autonomic nervous system of humans, the pulse rate continuously fluctuates around the average pulse level. The sympathetic nervous system accelerates the pulse level and the parasympathetic nervous system slows it down. The fluctuation, i.e. variation, of the pulse rate results from the operation of the cardiovascular control system. The primary variations are respiratory arrhythmia, variation caused by a baroreflex, and variation resulting from the adjustment of the temperature balance of the system.

Due to the attenuation caused by inhalation to the control of the vagus, the respiratory frequency is directly reflected in the pulse rate variation. Respiratory arrythmia has been found to be transmitted by the parasympathetic nervous system. In the experiments conducted, the parasympathetic nervous system has been paralysed with suitable pharmaceuticals, whereupon the frequency component corresponding to respiration in the frequency spectrum of the pulse rate is considerably attenuated.

The strength of the respiratory arrythmia depends both on the depth of respiration and the respiratory frequency. The maximum amplitude is obtained with the respiratory frequency of 5–7/minute, which is due to the fact that at this frequency the respiratory arrythmia and the pulse rate variation caused by the baroreflex arc intensify one another. When the respiratory frequency is increased but the depth of respiration remains constant, the respiratory arrythmia is attenuated with the slope:

$$0.75\text{–}1.5 \text{ log·min}^{-1}\text{·decade}^{-1} \tag{2}$$

However, the attenuation is individual, wherefore the values of respiratory arrhythmia at the respiratory frequencies of over 10/min are not mutually comparable. On the other hand, if the respiratory frequency is kept constant and the volume of respiration is increased from 0.5 liters to 3.0 liters, the amplitude of respiratory arrythmia increases. The increase is linear up to 50 to 60% of the individual respiratory capacity with the slope:

$$6\text{–}15/\text{min·l} \tag{3}$$

and it reaches its maximum value at the respiratory capacity of about 50%.

As the stress increases, the parasympathetic tone first decreases gradually. When the pulse rate reaches the level of about 100 beats/min, i.e. about 56% of the maximum pulse rate, the sympathetic activity starts increasing. Therefore, with a low stress the increase in the pulse rate is almost entirely due to the decreased parasympathetic activity. The sympathetic nervous system participates in the control of the pulse level together with the parasympathetic nervous system only at a higher stress level. However, the parasympathetic effect of the vagus decelerating the pulse remains during stress, even though it is greatly attenuated.

On the basis of the above, the following conclusions can be drawn:

the respiratory variation of the pulse rate also remains during stress, although greatly attenuated;

the respiratory frequency can be determined from the intervals between the location points of the pulse ECG signal by calculating the first-degree subtractions, filtering the frequencies exceeding 1 Hz from the obtained values, and by further calculating the respiration periods from the obtained graph during a certain time period, or by alternatively calculating the frequency spectrum of the filtered signal for example by means of Fourier transform, whereupon the respiratory frequency can be directly deduced from the resulting frequency response graph;

the threshold values for the energy metabolism of the system can be determined in most cases, and at least for the anaerobic threshold, by simultaneously measuring both the pulse rate and the respiratory frequency during an evenly increasing stress, and further by locating the discontinuities of the graph fr=fr(HR) formed from the obtained result pairs;

the accuracy of the threshold value determination can be improved at least in some cases by further combining the respiratory frequency determination with the respiratory volume per time (TV) on the basis of the degree of the pulse rate variation, the respiratory volume per time providing the ventilation graph VE=VE(HR) when combined with the values for respiratory frequency.

When the above-described conclusions are combined, it can be stated that on the basis of accurate pulse rate measurement it is possible to realize a system that automatically determines the threshold values for the energy metabolism of the user.

Figure 2:
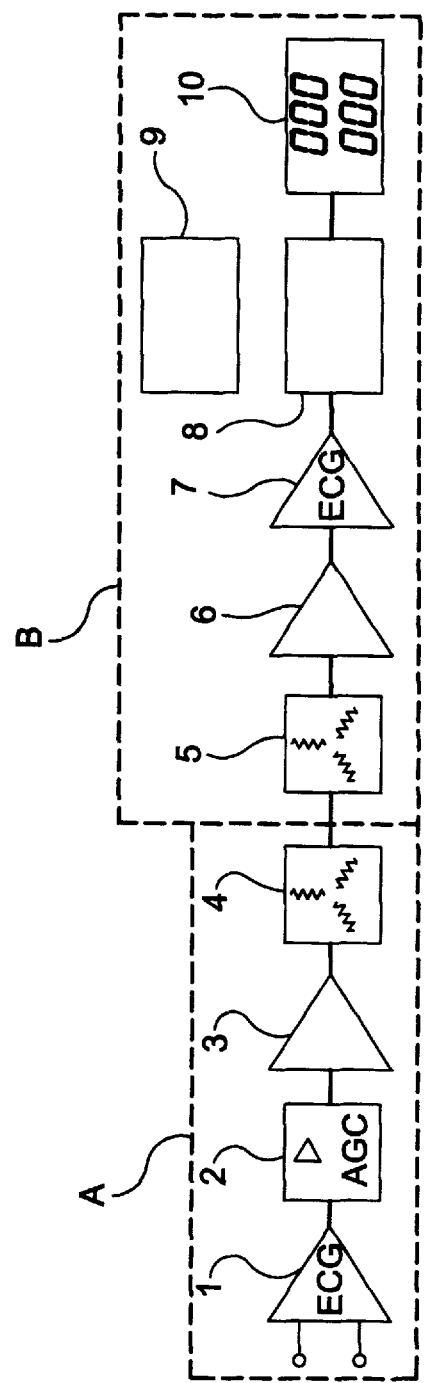
FIG. 2 shows a device according to the invention for determining threshold values for energy metabolism.

The equipment can be realized by means of modern technology with an accurate pulse rate measuring device. The method of analysing and calculating the measurement results is more difficult to realize. FIG. 2 shows an example of the pulse rate measuring apparatus to be applied in the invention; the principle of the apparatus, but not its calculating efficiency and/or principle, corresponds to the telemetric pulse rate measuring device disclosed in Finnish Patent 68,734. The pulse rate measuring device thus preferably consists of a pulse transmitter to be attached to the chest of the testee, and of a receiver wirelessly receiving pulse signals and comprising the functions of pulse rate measurement and analysis.

To be more exact, the equipment is formed, on the one hand, of a receiver A comprising an ECG preamplifier to which electrodes (not shown in the figures) identifying the pulse are connected. A signal from the preamplifier 1 is amplified in an AGC amplifier 2 and further in a power amplifier 3. The amplified signal is supplied to a transmission coil 4 that causes a magnetic field which is detected by a coil 5 of a receiver B forming the second part of the apparatus. The received signal is amplified similarly as in the transmitter by means of amplifier circuits 6 and 7. The amplified signal is supplied to a microprocessor 8 to which a memory 9 and a display unit 10 are connected.

In the apparatus according to the invention, the pulse rate measuring device measures the pulse rate of the testee continuously throughout the performance. The measurement is performed without the averaging that reduces the accuracy. The microprocessor 8 of the pulse rate measuring device with its software acts as an analyzer that differs from the previous averaging pulse rate measuring devices and that analyzes the ECG signal burst caused by each pulsation (cf. FIG. 1) in order to determine the maximum R. The microprocessor 8 also performs the necessary mathematical examinations (cf. formulas 2 and 3) on the basis of the R—R variation in order to calculate the respiratory frequency curve of the testee as a function of the pulse rate during the performance. Finally, it determines the threshold values for the energy metabolism of the testee from the discontinuities of the respiratory frequency curve and shows them on the display unit 10. The discrimination ability of the pulse rate measuring device in the determination of the intervals between the maximums of successive ECG signal bursts is preferably at least around 1 ms.

Figure 3:
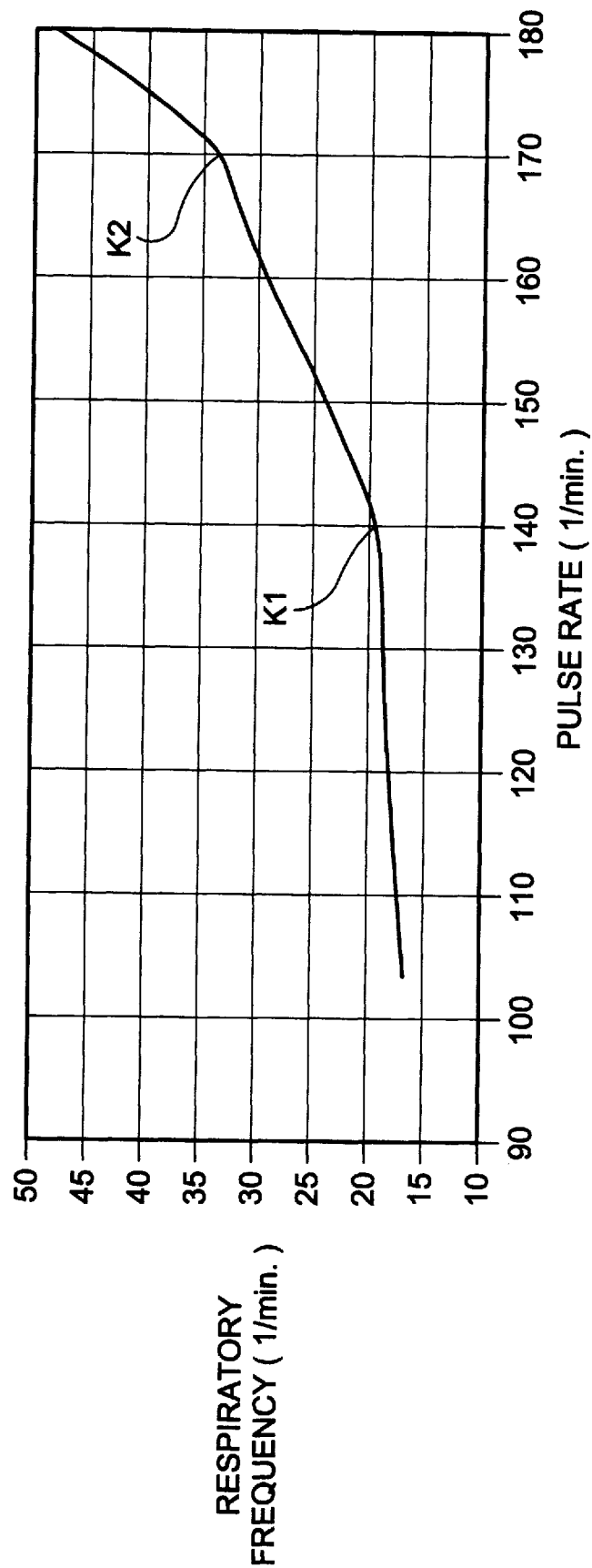
FIG. 3 shows a respiratory frequency, determined according to the invention on the basis of the variations in the intervals between the maximums of the ECG signal bursts of the pulse, as a function of the pulse level.

FIG. 3 shows results of a test measuring, with the accuracy of 1 ms, the intervals between the maximums of the ECG signal bursts during the stress test of a testee, performed with an ergometer (stationary bicycle). Respiration events and the rate of their occurrence were determined from the obtained intervals with a mathematical method based on the above-described interdependencies of respiration and pulse rate. The graph of FIG. 1 shows the discontinuity K1 of the respiratory frequency at the pulse rate of 140/min, which is the aerobic threshold of the testee. The anaerobic threshold K2 of the testee is at the pulse level of about 170/min.

It is clear for a person skilled in the art that the different embodiments of the invention are not restricted to the above-described example, but they may vary freely within the scope of the appended claims.

What is claimed is:

1. A method for determining threshold values for a person's energy metabolism, in which method a testee is subjected to a gradually increasing stress in order to obtain the threshold values for his energy metabolism, characterized by the method comprises the following steps of a) measuring the pulse rate of the testee during the performance;

b) analysing the pulse shape of an ECG signal caused by the pulse in order to determine the timing point of the ECG signal corresponding to each pulsation, and determining the intervals between the timing points of successive ECG signals;

c) calculating the respiratory frequency of the testee on the basis of the variations in the intervals between the timing points of the ECG signals, and calculating the respiratory frequency of the testee as a function of the pulse rate during the performance;

d) determining at least one threshold value for the energy metabolism of the testee on the basis of the respiratory frequency and the pulse rate.

2. A method for determining threshold values for a person's energy metabolism, in which method a testee is subjected to a gradually increasing stress in order to obtain the threshold values for his energy metabolism, characterized by the method comprises the following steps of a) measuring the pulse rate of the testee during the performance;

b) analysing the pulse shape of an ECG signal caused by the pulse in order to determine the timing point of the ECG signal corresponding to each pulsation, and determining the intervals between the timing points of successive ECG signals;

c) calculating the respiratory frequency of the testee on the basis of the variations in the intervals between the timing points of the ECG signals;

d) estimating the respiratory volume of the testee on the basis of the degree of the variation in the timing points of the ECG signals;

e) calculating the ventilation of the testee as a function of the pulse rate on the basis of the respiratory frequency calculated during the performance and the estimated respiratory volume.

f) determining at least one threshold value for the energy metabolism of the testee on the basis of the calculated ventilation and the pulse rate.

3. A method according to claim 1 or 2, characterized by the timing point of the ECG signal of the testee's pulse and the intervals between the timing points of successive ECG signals are determined on the basis of the R—R peak values of the ECG signals.

4. A device for determining threshold values for a person's energy metabolism, in which device a testee is subjected to a gradually increasing stress in order to obtain the threshold values for his energy metabolism, characterized by the device consists of a pulse rate measuring device which measures the pulse rate of the testee during the performance, and of an analyzer which is contained in the pulse rate measuring device, which analyses the pulse shape of the ECG signal caused by each pulsation in order to determine the timing point of the ECG signal and performs predetermined mathematical examinations to determine the intervals between the timing points of successive ECG signals, in order to calculate the respiratory frequency of the testee on the basis of the variations in the intervals between the timing points of the ECG signals as a function of the pulse rate during the performance, and which determines at least one threshold value for the energy metabolism of the testee on the basis of the respiratory frequency and the pulse rate.

5. A device for determining threshold values for a person's energy metabolism, in which device a testee is subjected to a gradually increasing stress in order to obtain the threshold values for his energy metabolism, characterized by the device consists of a pulse rate measuring device which measures the pulse rate of the testee during the performance, and of an analyzer which is contained in the pulse rate measuring device, which analyses the pulse shape of the ECG signal caused by each pulsation in order to detect the timing point of the ECG signal and performs predetermined mathematical examinations to determine the intervals between the timing points of successive ECG signals, in order to calculate the respiratory frequency of the testee on the basis of the variations in the intervals between the timing points of the ECG signals, which estimates the respiratory volume of the testee on the basis of the degree of the variations in the timing points of the ECG signals, which calculates the ventilation of the testee on the basis of the respiratory frequency and the respiratory volume as a function of the pulse rate during the performance, and which determines at least one threshold value for the energy metabolism of the testee on the basis of the calculated ventilation and the pulse rate.

6. A device according to claim 4 or 5, characterized by the device is based on an accurate pulse rate measuring device, the discrimination ability of the device in the determination of the intervals between the timing points of successive ECG signals being at least around 1 ms.

7. A device according to claim 6, characterized by the pulse rate measuring device consists of a pulse transmitter to be attached to the chest of the testee and of a receiver wirelessly receiving pulse signals, the receiver comprising the functions of pulse rate measurement and analysis.

* * * * *

UNITED STATES PATENT AND TRADEMARK OFFICE
CERTIFICATE OF CORRECTION

PATENT NO.   :   5,810,722
DATED        :   September 22, 1998
INVENTOR(S)  :   Heikkilä

It is certified that error appears in the above-identified patent and that said Letters Patent is hereby corrected as shown below:

In Column 7, Line 21,           the patent now reads "signals are determined"
                                this should read --signals being determined--

In Columm 7, line 14,           the patent now reads "volume."
                                this should read --volume, and--

In Column 6, Line 63,           the patent now reads "method comprises the"
                                this should read --method comprising the--

In Column 6, Line 42,           the patent now reads "method comprises the"
                                this should read --method comprising the--

Signed and Sealed this

Sixteenth Day of February, 1999

Attest:

Attesting Officer

*Acting Commissioner of Patents and Trademarks*